(12) United States Patent
Oral et al.

(10) Patent No.: US 9,011,551 B2
(45) Date of Patent: Apr. 21, 2015

(54) MULTIMODALITY LEFT ATRIAL APPENDAGE OCCLUSION DEVICE

(75) Inventors: Hakan Oral, Ann Arbor, MI (US); Fred Morady, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 187 days.

(21) Appl. No.: 13/546,662

(22) Filed: Jul. 11, 2012

(65) Prior Publication Data

US 2013/0018413 A1  Jan. 17, 2013

Related U.S. Application Data

(60) Provisional application No. 61/506,405, filed on Jul. 11, 2011.

(51) Int. Cl.
| | | |
|---|---|---|
| A61F 2/02 | (2006.01) | |
| A61B 5/00 | (2006.01) | |
| A61B 17/12 | (2006.01) | |
| A61N 1/372 | (2006.01) | |
| A61B 17/00 | (2006.01) | |

(Continued)

(52) U.S. Cl.
CPC ......... *A61B 5/0031* (2013.01); *A61B 17/12122* (2013.01); *A61N 1/37205* (2013.01); *A61B 17/0057* (2013.01); *A61B 17/12131* (2013.01); *A61B 17/12136* (2013.01); *A61B 17/12172* (2013.01); *A61B 17/12186* (2013.01); *A61B 5/0006* (2013.01); *A61B 5/0008* (2013.01); *A61B 5/0215* (2013.01); *A61N 1/057* (2013.01); *A61N 1/37264* (2013.01); *A61N 1/37258* (2013.01); *A61B 2017/00022* (2013.01); *A61B 2017/00084* (2013.01); *A61B 2017/00579* (2013.01); *A61B 2017/00588* (2013.01); *A61B 2017/00597* (2013.01); *A61B 2017/00606* (2013.01); *A61B 2017/0061* (2013.01); *A61B 2017/00615* (2013.01); *A61B 2017/00632* (2013.01); *A61B 2017/0065* (2013.01)

(58) Field of Classification Search
USPC .......................... 606/213; 600/302; 623/23.72
See application file for complete search history.

(56) References Cited

U.S. PATENT DOCUMENTS

| | | |
|---|---|---|
| 4,007,743 A | 2/1977 | Blake |
| 6,551,303 B1 | 4/2003 | Van Tassel et al. |
| 6,941,169 B2 | 9/2005 | Pappu |

(Continued)

FOREIGN PATENT DOCUMENTS

WO  WO-2010/085659 A1  7/2010

OTHER PUBLICATIONS

International search report and written opinion from International Application No. PCT/US12/046256 dated Nov. 29, 2012.

*Primary Examiner* — Victor Nguyen
(74) *Attorney, Agent, or Firm* — Marshall, Gerstein & Borun LLP

(57) ABSTRACT

A left atrial appendage occlusion device is provided that acts in conjunction with a wireless transponder unit. The occlusion device provides a seal of the left atrial appendage opening, while the transponder is inserted into the left atrial appendage to sense one or more physiological conditions and relay the sensed information over wireless communication. Further, all or part of the left atrial appendage may be filled using a biocompatible inert filling material injected into the left atrial appendage as part of deployment of the transponder unit.

15 Claims, 13 Drawing Sheets

(51) Int. Cl.
*A61B 5/0215* (2006.01)
*A61N 1/05* (2006.01)

(56) References Cited

U.S. PATENT DOCUMENTS

| | | | |
|---|---|---|---|
| 7,288,090 B2 | 10/2007 | Swanson | |
| 7,455,669 B2 | 11/2008 | Swanson | |
| 7,566,336 B2 | 7/2009 | Corcoran et al. | |
| 7,801,626 B2 * | 9/2010 | Moser | 607/126 |
| 7,824,397 B2 | 11/2010 | McAuley | |
| 2003/0195555 A1 | 10/2003 | Khairkhahan et al. | |
| 2004/0034366 A1 | 2/2004 | van der Burg et al. | |
| 2004/0127935 A1 | 7/2004 | VanTassel et al. | |
| 2005/0049573 A1 | 3/2005 | Van Tassel et al. | |
| 2005/0065589 A1 | 3/2005 | Schneider et al. | |
| 2005/0228468 A1 | 10/2005 | Macoviak et al. | |
| 2005/0277680 A1 | 12/2005 | Priebe et al. | |
| 2006/0149314 A1 | 7/2006 | Borillo et al. | |
| 2007/0032734 A1 | 2/2007 | Najafi et al. | |
| 2009/0005656 A1 | 1/2009 | Najafi et al. | |
| 2009/0088836 A1 * | 4/2009 | Bishop et al. | 623/2.1 |
| 2009/0182206 A1 | 7/2009 | Najafi et al. | |
| 2013/0116724 A1 | 5/2013 | Clark et al. | |
| 2013/0190799 A1 | 7/2013 | Clark | |
| 2013/0237908 A1 | 9/2013 | Clark | |

\* cited by examiner

MULTIMODALITY LEFT ATRIAL APPENDAGE OCCLUSION DEVICE

CROSS REFERENCE TO RELATED APPLICATION

The present application claims the benefit of U.S. Provisional Application No. 61/506,405, entitled "Multimodality Left Atrial Appendage Occlusion Device," filed on Jul. 11, 2011, which is hereby incorporated by reference herein in its entirety.

FIELD OF THE INVENTION

The present invention relates generally to devices for analysis and treatment of the heart and more particularly to a multimodality device for left atrial appendage occlusion.

BACKGROUND OF THE RELATED ART

Atrial fibrillation (AF) is the leading cause of strokes due to thrombi (e.g., blood clots) that predominantly form in the left atrial appendage (LAA) and then subsequently embolize.

There are, of course, a number of treatments to prevent, or more accurately reduce the risk of, stroke. But the treatments are lacking. For example, although systemic anticoagulation using warfarin has been used to minimize the risk of stroke, warfarin is nonetheless associated with a 0.5-1% per year risk of major bleeding including intracranial bleeding. Furthermore, not all patients are eligible to take warfarin due to risk of bleeding. More importantly, patients at highest risk for strokes often are also at highest risk of bleeding and cannot take warfarin.

There is need for a device that will effectively prevent thrombi formation and embolism, and preferably provide additional functionality to treat a patient experiencing AF.

SUMMARY OF THE INVENTION

The present application describes an apparatus that hinders or even prevents thrombus buildup in the first instance. The apparatus not only occludes the LAA, the apparatus eliminates the potential space within the LAA where thrombus formation could form. Numerous examples are described, but principally, an occlusion device is used to block the orifice opening of the LAA, i.e., the ostium, where the occlusion device is configured to allow injection of a biocompatible, inert material into the LAA during implantation. This material is used to fill the LAA acting as a bulking agent. The material may be injected directly into the LAA or in an expandable balloon within the LAA and is maintained in a liquid phase during implantation, which allows the material to better fill the entire LAA volume. In some examples, the occlusion device caps the fluid preventing it from spilling out of the LAA, and thus avoiding the possibility of embolism. In other examples, the fluid levels are monitored during insertion to prevent spillover. Either way, preferably the material is maintained in the liquid phase throughout insertion and then actively converted it into a solid phase by a controllable mechanism, such as application of a catalyst material into the LAA that induces a solid phase in the material or application of an electrical current, radiofrequency energy, heat, light, etc that solidifies the material. In other examples, the transition from liquid phase to solid phase occurs naturally over time, in response to body temperature, or in response to blood entering the LAA. In some examples, the biocompatible, inert material is conductive.

The device includes a delivery catheter through which the apparatus is deployed, including the occlusion device and the inert material. The occlusion device may take the form of an umbrella, butterfly or a balloon design to include the orifice of the LAA during deployment.

In some examples, the apparatus also includes a MEMS transponder unit, which is deployed into the LAA before, during, or after injection of the biocompatible material, and then retained in the material after hardening to the solid phase. The transponder serves to record and transmit electrical activity of the LAA, either through conductive media or by direct contact to the LAA wall. The transponder may record electrical activity and electrograms, pressure, transthoracic impedance, temperature, pH, oxygen saturation. The recorded values are then transmitted wirelessly to an interface communications device, which may be located internally, within the body, or external to the body, and which performs pre-processing on the signals from the transponder, such as, bandwidth filtering, noise reduction, and signal amplification. In some examples, the interface device performs preliminary analysis of the received signal, e.g., converting raw signal data into numerically representative form.

The transponder is preferably self-powered, through a rechargeable power unit that may be recharged inductively using the interface device or other device.

An embodiment of the present invention is an implantable apparatus for blocking a left atrial appendage, the apparatus comprising: an occlusion device having a positioning stage in which the occlusion device is collapsed for positioning the occlusion device at an opening of the left atrial appendage, the occlusion device having a cover that in a deployed stage encloses the opening and a strut support structure that in a deployed stage fixedly engage the cover to enclose the opening; and a transponder unit configured to sense a physiological condition, the transponder unit having a wireless transmitter for transmitting reporting signals indicating the sensed physiological condition, the transponder unit is connected to the strut support structure such that in the deployed stage the strut support structure maintains engagement with the transponder unit and positions the transponder unit within the left atrial appendage for sensing the physiological condition within the left atrial appendage.

In another embodiment, an implantable apparatus for blocking a left atrial appendage comprises: an occlusion device having a positioning stage in which the occlusion device is collapsed for positioning the occlusion device at an opening of the left atrial appendage, the occlusion device having a cover that in a deployed stage encloses the opening and a strut support structure that in a deployed stage fixedly engages the cover to enclose the opening; a transponder unit configured to sense a plurality of physiological conditions and configured to wirelessly transmit sensed measurements of the physiological conditions to an external receiver; and a biocompatible, inert material in liquid phase inserted into the left atrial appendage, wherein the biocompatible, inert material freely suspends the transponder unit within the left atrial appendage.

The features, functions, and advantages can be achieved independently in various embodiments of the present invention or may be combined in yet other embodiments.

DESCRIPTION OF DETAILED EXAMPLES

Figure 1:
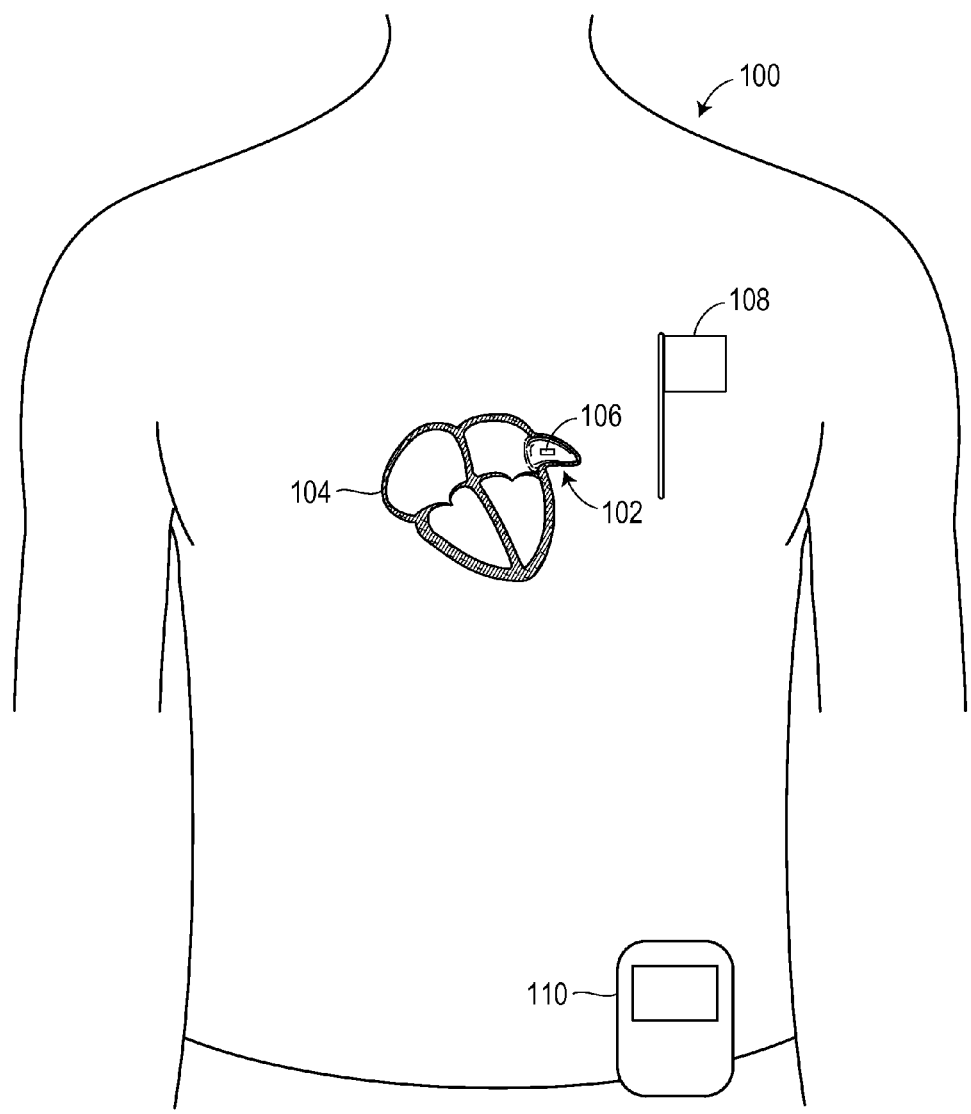
FIG. 1 illustrates an implantable apparatus for blocking the left atrial appendage, showing an implanted transponder, interface communication unit, and portable control device, in accordance with an example.

FIG. 1 illustrates an implantable apparatus 100 for blocking a left atrial appendage 102 of the heart 104. The apparatus includes an implanted transponder unit 106, an interface communication unit 108, and portable control device 110.

The transponder unit 106 has a sensing mode in which the device senses one or more physiological conditions that are detectable within the LAA. Different embodiments will provide sensing of one or more physiological conditions. These physiological conditions include rhythm of the atria, pressure, transthoracic impedance, temperature, oxygen saturation, pH, etc.

A sensing mode that senses pressure within the LAA indicates left ventricular filling pressures. Analyzing these pressure measurements, healthcare professionals may diagnose whether the patient is developing heart failure or there is contractile dysfunction of the heart.

A sensing mode that senses transthoracic impedance indicates the impedance across the chest wall. This impedance is reduced with fluid build up in the lungs and thus suggestive of heart failure. The sensed impedance may be automatically or manually compared to previous impedance measurements, for example, to determine change over time.

A sensing mode that sensing temperature indicates core body temperature. From the measurement, healthcare professionals may diagnose any febrile illness.

A sensing mode that records electrograms within the LAA can enable immediate diagnosis of whether the patient is in sinus rhythm or AF. In some examples, the transponder unit 106 senses heart rhythms longitudinally so that arrhythmia burden can be defined over a period of time. The data may be stored on an optional local memory 179 of the transponder unit 106, see FIG. 2A, or may be stored in a remote interface or controller as discussed further below.

In the illustrated example, the transponder unit 106 is a multimodal device capable of sensing in each mode. The sensing measurements may be made at periodic intervals, but are typically performed continuously. Furthermore, a control unit 110 with the transponder unit 106 is programmed to automatically alert the patient and/or physician if any of the measured physiological conditions reach a threshold level or otherwise indicate a warning condition for the patient. Such automatic detection and alert, based on the measured values from the transponder unit 106, is valuable because ~30% of patients with AF may be asymptomatic. Timely diagnosis of AF can be critically important to prevent thromboembolic complications such as stroke, unnecessary treatment with blood thinners which can lead to major potentially fatal bleeding complications and prevention of heart failure due to rapid rates during AF.

Figure 2A:
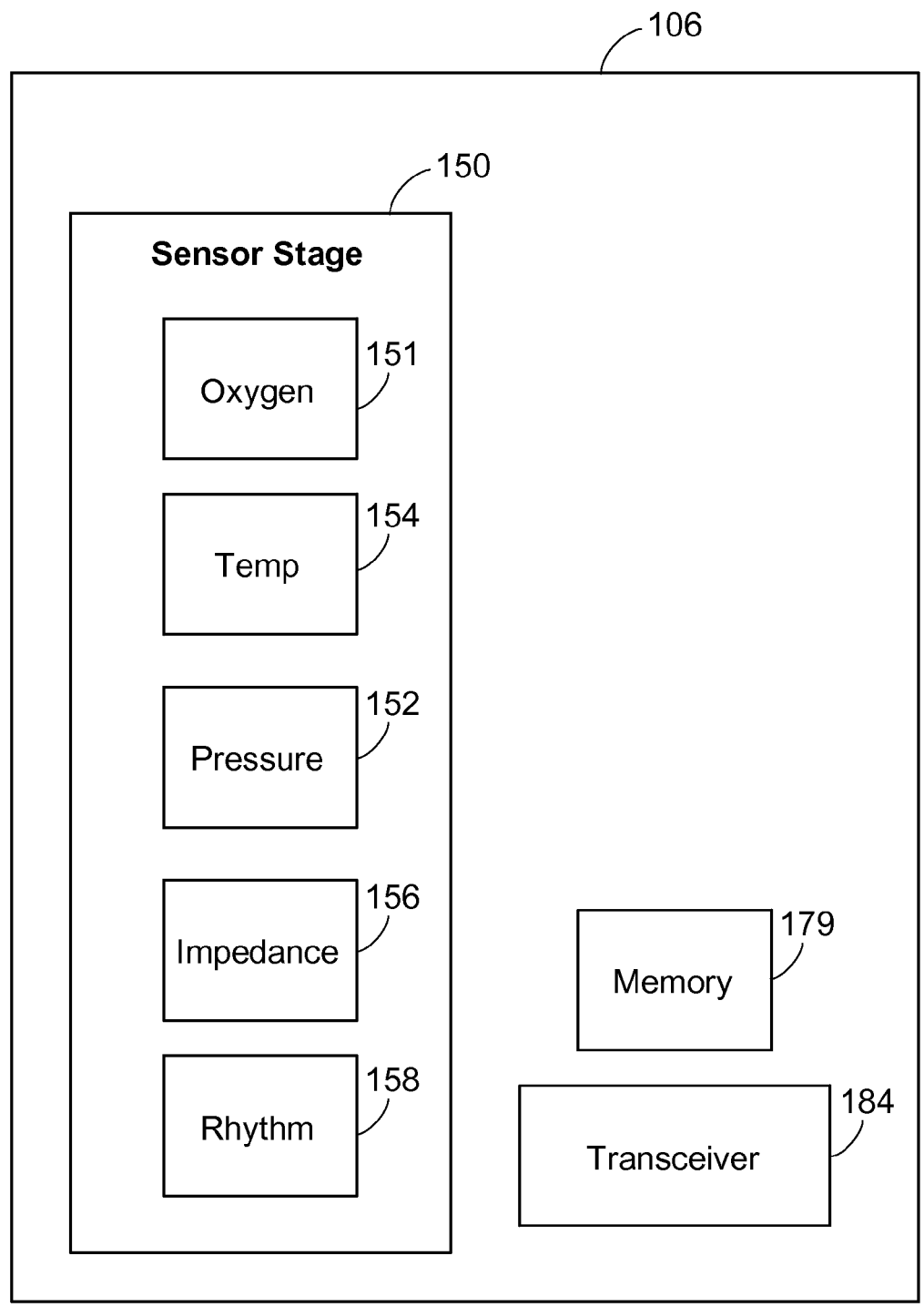
FIG. 2A is block diagram of an example transponder unit as may be used in the implantable apparatus of FIG. 1.

As shown in FIG. 2A, the transponder unit 106 includes a sensor stage 150 that is able to sense one or more physiological conditions within the LAA. That sensor stage may perform electrical monitoring of electrically-determined physiological conditions and/or monitoring for hemodynamically-determined physiology conditions (pressure, etc.). The sensor stage may for example include a MEMS/NEMS fabricated oxygen content/saturation filter 151, a MEMS/NEMS fabricated pressure sensor 152, a MEMS/NEMS fabricated temperature sensor 154, and an MEMS/NEMS fabricated impedance measuring sensor 156, and a MEMS/NEMS fabricated rhythm sensor 158. The latter may be include capability to record, filter, amplify, process and transmit electrograms. As used herein MEMS refers to Micro Electromechanical Systems; and NEMS refers to Nano Electromechanical Systems. For both known fabrication techniques suitable to form the devices described herein are contemplated.

The transponder under 106 communicates with the communication interface unit 108, which may be external to the patient, for example on a belt etc., or alternatively may be implanted internally within the patient, as shown in FIG. 1. Either way the interface unit 108 includes a transceiver and wirelessly communicates with the transponder unit, in particular transceiver 184 (184') of the transponder unit 106. The transceiver 184 communicates the sensed reporting signals, corresponding to the sensed measured values, to the interface unit 108. These include measurements of any of physiological conditions mentioned herein.

The unit 108 may communicate the received reporting signals from the transponder unit 106 to the control device 110, after signal amplification, noise reduction, any pre-filtering, and any preliminary data analysis. That communication may be wireless or through a wired means, such as through a universal serial bus (USB) connection to the control device 110.

The control device 110 may be a dedicated handheld, portable device displaying physiological conditions, such as pressure, temperature, and/or impedance. The device 110 may display rhythm data for the heart as well. The device 110 can display any of the sensed data from the transponder unit 106.

The wireless communications may be implemented using any standard protocol or specification, such as WiFi or any of the Institute of Electrical and Electronics Engineers (IEEE) 802.11 a, b, g, or n standards, Bluetooth™, Near Field Communication, radio-frequency identification (RFID) or others. The wireless communication may alternatively be implemented using a proprietary protocol.

In some examples, the device 110 analyzes the received sensed signals and determines the physiological condition of the patient, such as the rhythm status, sinus rhythm (SR) and AF. The device 110 also determines alarm conditions that can alert the patient and physician or other care provider, where such alarm conditions are displayed to the patient or care provider. A treatment instruction or instruction regimen can be prepared in response to the analysis of the device 110. In some examples, the device 110 is programmed to present actual instructions on a screen as to how to address the alarm condition.

The control device 110 may indeed be a stand-alone wireless device or incorporated into an existing system, such as a pacing/defibrillation system.

Figure 2B:
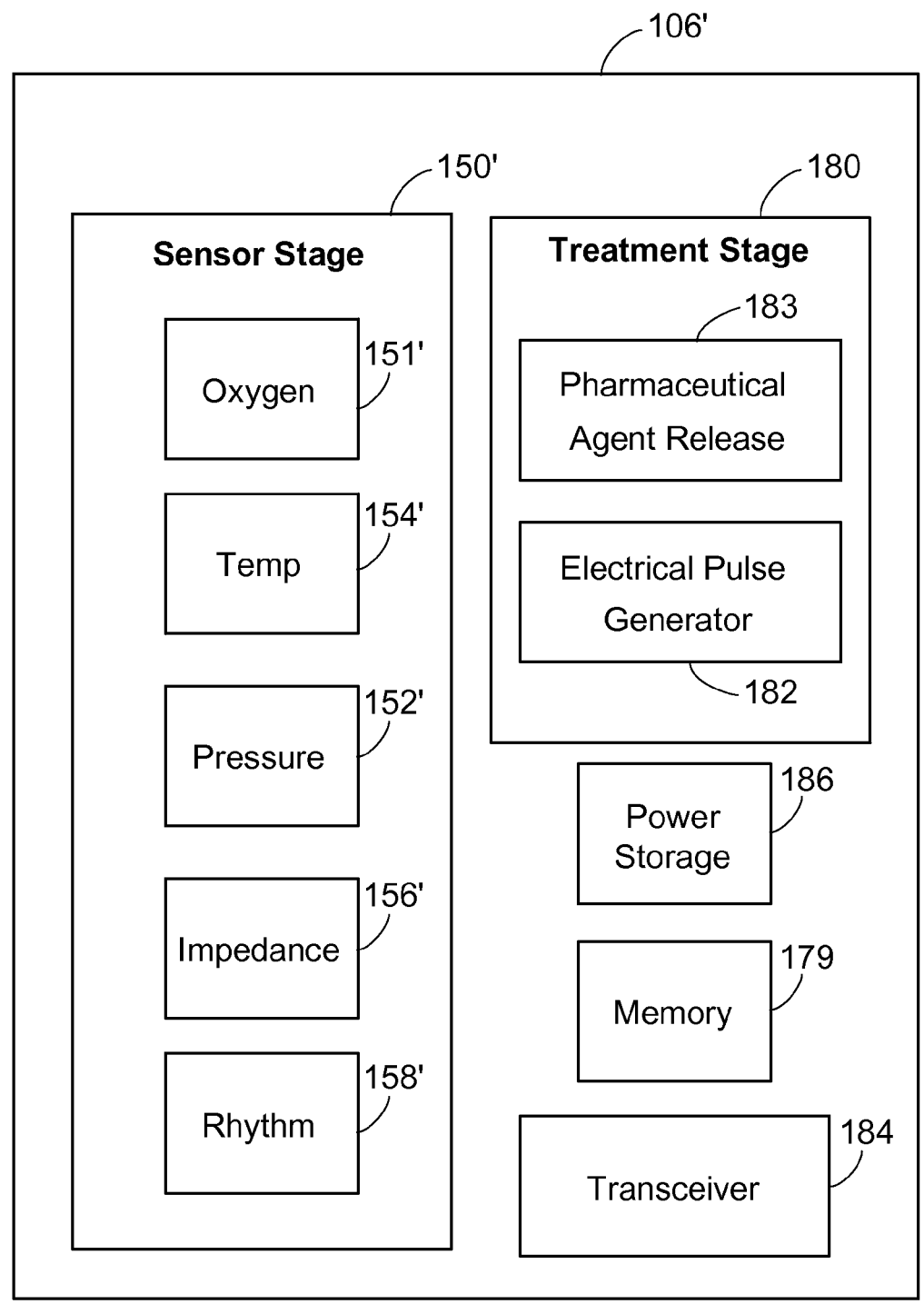
FIG. 2B is block diagram of another example transponder unit as may be used in the implantable apparatus of FIG. 1.

In some examples, the transponder unit is a multi-mode device, which in addition to the sensing mode capabilities described above, optionally includes a treatment mode, in which the device is able to treat conditions in the LAA or in the heart, more generally, such as atrial fibrillation or atrial flutter. In FIG. 2B, the transponder unit 106' is shown having similar elements to those of FIG. 2A and also including a treatment stage 180 that, in the illustrated example, includes an electrical pulsing stage 182, which is used to apply an electrical pulse to the heart in response to a sensed atrial fibrillation condition or bradycardia (slow heart rate) condition such as may occur after conversion of AF to sinus rhythm sensed by the stage 150'. The transponder unit 106' further includes another treatment device in the form of a pharmaceutical agent release stage 183, which releases a pharmaceutical agent into the left atrial appendage for treatment of AF or heart failure or otherwise as determined from the sensor data from the sensor stage 150'.

In some examples, the pulse stage 182 and the pharmaceutical agent release stage 183 are part of a control system in which, the sensor stage 150' determines one or more physiological conditions indicating, either alone or when combined with other condition data, an arrhythmia condition. In that control system, the sensor stage 150' then communicates the sensed signals to the communication interface 108, which then analyzes the signals to determine if an arrhythmia condition exists.

While the control system of FIG. 2B may be an open loop system, in other examples, the control system is a closed loop system where the sensor stage 150' constantly senses the one or more physiological conditions and feeds the sensed signals into the interface 108 or control device 110 (of FIG. 1), which constantly update the treatment signals communicated to the treatment stage 180. Such control loop adjustment may occur at predetermined time intervals, for example, to achieve constant adjustment.

Figure 3A:
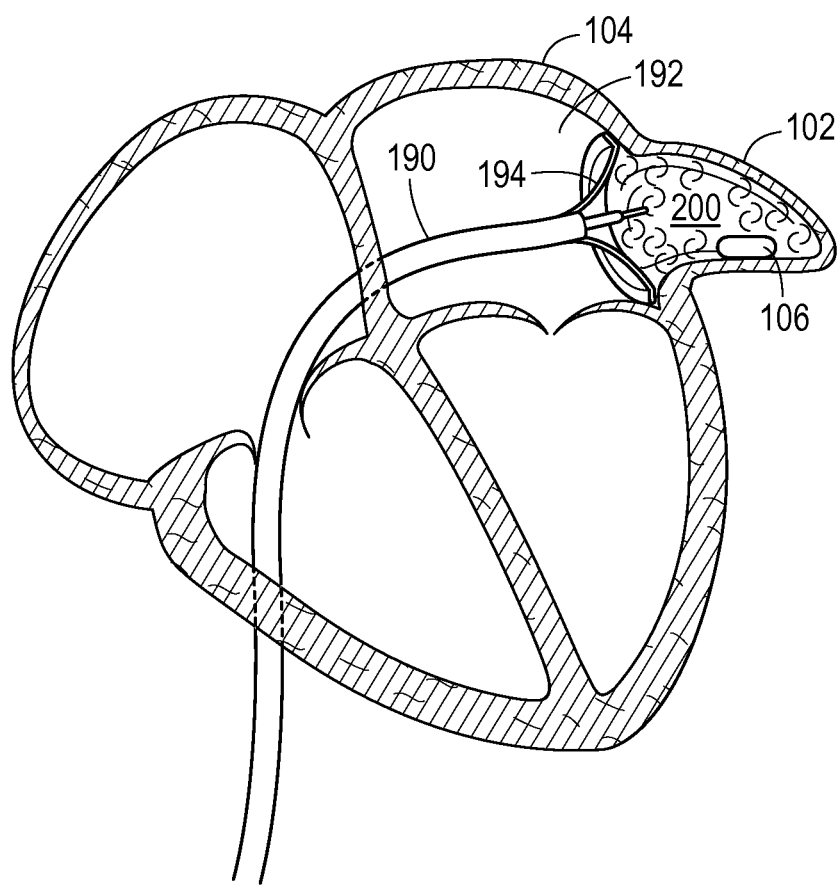
FIG. 3A illustrates the deployment stage of an implantable apparatus for blocking the left atrial appendage, with the apparatus implanted in direct contact with an inner wall of the LAA.
Figure 3B:
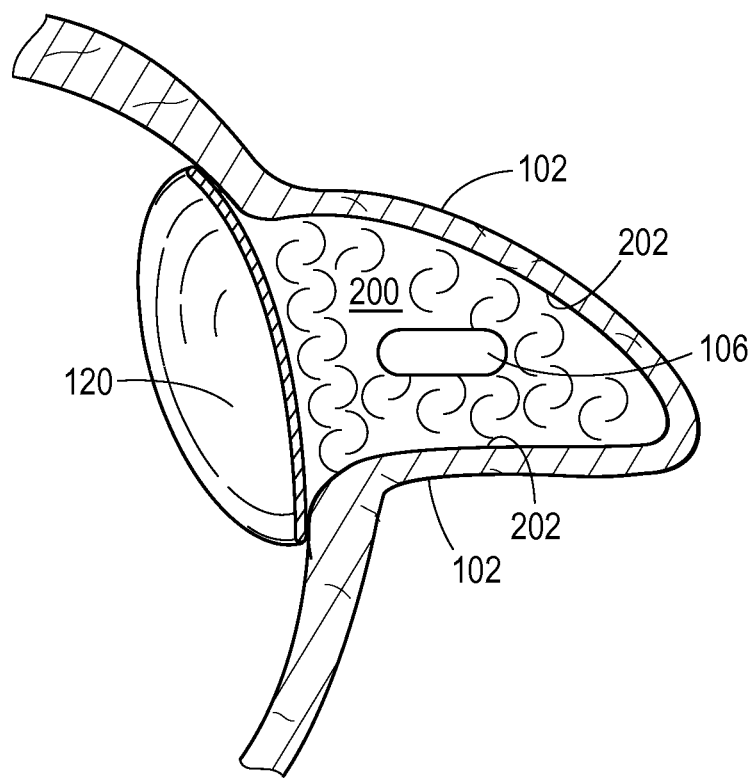
FIG. 3B illustrates the deployment stage of an implantable apparatus for blocking the left atrial appendage, with the apparatus implanted suspended within the LAA out of direct contact with an inner wall.

To facilitate both sensing and treatment, the transponder 106/106' may be placed within the LAA using a conductive element. First, as shown in the example of FIG. 3B (discussed further below), when the transponder unit 106—unit 106' though not shown would be used in the illustrated example the same way—is suspended within the LAA 102, then a biocompatible, inert filler material 200 injected into the LAA 102 may be conductive, such that the sensor may sense a signal through or an electrical pulse generate may produce a signal through the material 200 to the inner walls 202 of the LAA 102.

Figure 3C:
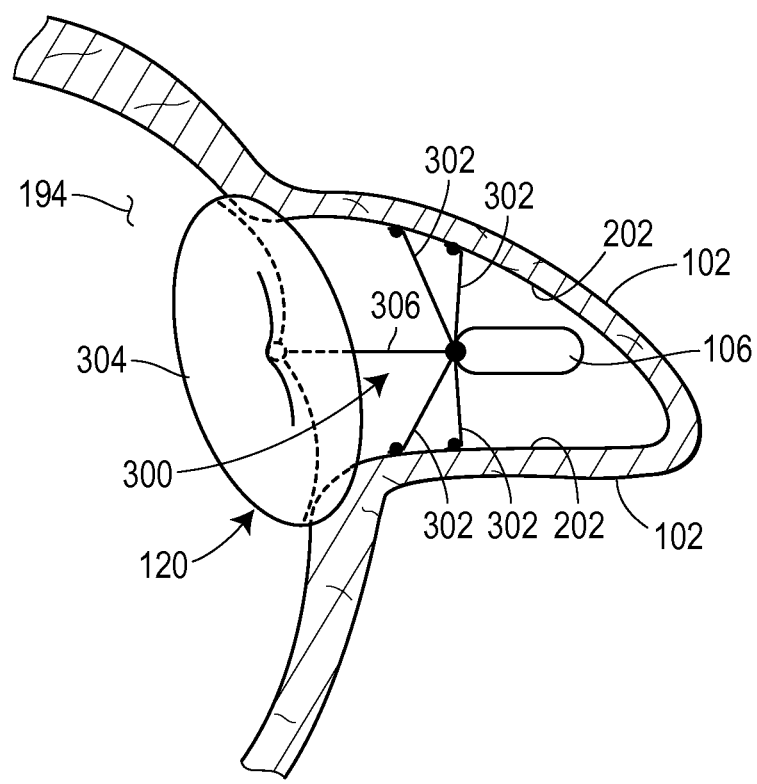
FIG. 3C illustrates the deployment stage of an implantable apparatus for blocking the left atrial appendage, with the apparatus implanted suspended in the LAA by a strut support structure of an occlusion device.

FIG. 3C, the transponder unit 106 is supported by a strut support structure 300 which has conductive struts 302 extending from the transponder 106 to the walls of the LAA 102, such that sensing is from or treatment is applied to the walls of the LAA through struts 302. In the illustrated example these conductive struts 302 are also anchoring struts that engage the inner wall 202 of the LAA 102 and retain the transponder unit 106 without direct contact.

Figure 3D:
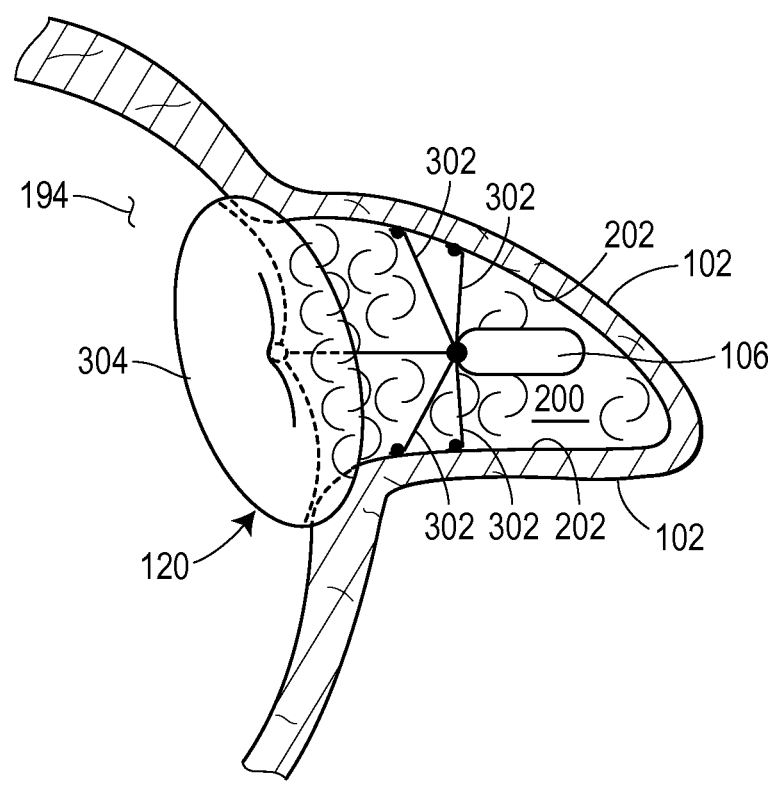
FIG. 3D illustrates another example of the deployment stage of an implantable apparatus for blocking the left atrial appendage.

FIG. 3D illustrates a similar configuration to that of FIG. 3C, but with both struts 302 and the inert material 200 supporting the transponder unit 106 within the LAA 102.

In some examples, the transceiver 184 receives treatment instructions signals from the unit 108 for controlling one or both of the electrical pulse generator 182 and the pharmaceutical agent release stage 183.

The transponder unit 106 includes an inductive power storage 186 which powers the unit 106 and which may be recharged by the interface unit 108 through an inductive recharging. In such a configuration, the unit 108 may be battery powered, for example.

In some examples, the charging is achieved through radiofrequency induction, which may use a frequency of 125 MHz. For example, the passive power mechanism may be implemented by having the interface unit 108 interrogate the transponder unit 106 for new measurements using a poll signal.

Figure 4:
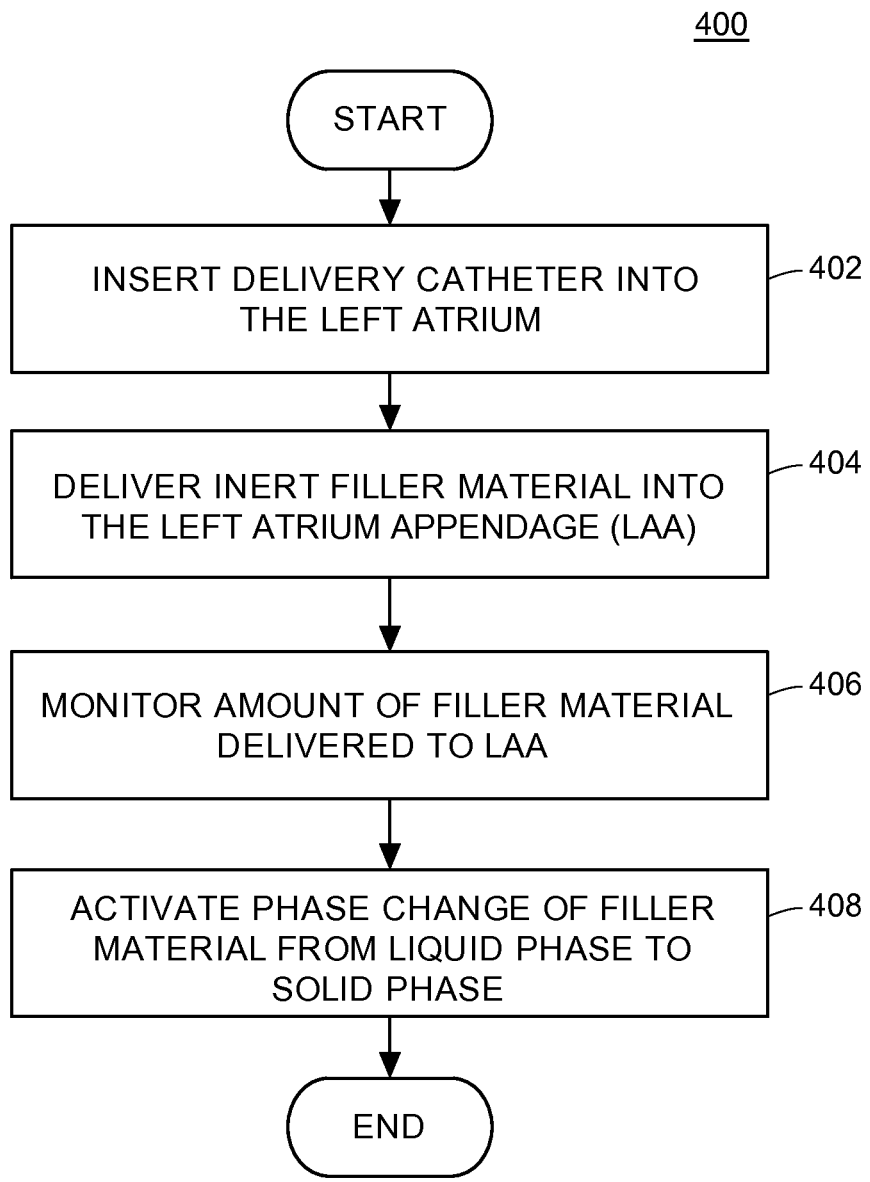
FIG. 4 illustrates a process for deploying an implantable apparatus for blocking the left atrial appendage.

FIG. 4 is a process 400 used to deploy the transponder unit 106. At an initial block 402, insertion of a delivery catheter occurs. First a transeptal puncture is made using either one of the conventional catheter systems or using the delivery sheath, and dilator included in this description. If a conventional transeptal sheath is used, this is later exchanged with delivery sheath described herein using over the wire technique once the transeptal puncture and access to the left atrium is obtained. Then the delivery system that includes a delivery sheath through which a delivery catheter, such as catheter 190 in FIG. 3A, is positioned into the left atrium 192, the catheter 190 may be a 8-14 Fr sized catheter. Once the catheter 190 is positioned in place, with a distal end extending into the left atrium, the transponder unit 106, the material 200, and an occlusion device 194 (shown in FIG. 3A) may be implanted.

As shown in FIG. 4, with the delivery catheter in position, at a block 404, a biocompatible, inert material is injected into the LAA to serve as a volume filler material, such as the material 200. To deliver the material 200, the delivery catheter 190 may be used with a dedicated delivery lumen formed inside the catheter 190.

In this initial stage of the process, the material 200 is in a liquid phase form and has not been converted to a solid phase. Preferably the material is maintained in this liquid phase throughout injection into the LAA 102, thereby allowing the material 200 to better fill the entire LAA volume.

The material 200 is preferably biocompatible and inert, which means that it will not adversely affect conditions in the LAA or the blood flow system if introduced in the blood circulation. The inert biocompatible material 200 may be, for example, silicone oil, a variety of polymers, polyethylene, polyester, and expanded polytetrafluoroethylene, PET, ePET, biomimetic hydrogels, polyvinyl alcohols (PVA), polycaprolactone, ovalbumin, biocompatible hydrogels, collagen, alginate hydrogel, polyethylene glycol, fibrin glue, poly(2-hydroxyethyl methacrylate) (PHEMA) and poly N-(2-hydroxypropyl)-methacrylamide (PHPMA), liquid embolic materials such as isobutyl-2 cyanoacrylate, and particulate embolic material such as spheres coated with iron or barium, or silicone particles, N-butyl cyanoacrylate (NBCA) (that hardens a soon as it gets in contact with blood or ionic material such as saline) polyvinyl alcohol sponge (PVA), gelfoam, ethanol or other alcohols, or microcoils. Other biocompatible, inert materials may also be used. However, it may be desirable to prevent that material from exiting the LAA during this initial injection stage. Therefore, the amount of material 200 introduced into the LAA 102 may be monitored against leakage of the biocompatible material. This material can also be radio-opaque or echogenic so that delivery of the material can be monitored by X-ray or ultrasound (intracardiac, transesophageal or surface echocardiography).

To monitor the amount of material 200 delivered to the LAA 102, more specifically to monitor the fluid levels and prevent leakage, at a block 406, an RCA (radio contrast agents), i.e., radiopaque dye, may be used in the material to visually indicate if there is leakage. An x-ray imaging system will be able to display RCA and thereby identify if any of the material is escaping the LAA. Other visualizable media may be introduced instead. In either example, the delivery catheter may contain a deliver lumen or capillary used to introduce the agent from the catheter to the material trapped in the LAA. In another example, an intracardiac ultrasound (or some other ultrasound) may be used to visualize the material, relying upon the difference in density of the injected material versus that of the heart tissue. An example is a transesophageal ultrasound device, which when inserted into the esophagus can be used for highly identifiable imaging of the left atrium. In any event, these techniques may be particularly useful as they are also often used for catheter positioning anyway.

Various biocompatible, inert compositions may be used for the material 200. These include classes of materials, such as various polymers.

While example classes of materials are described, it will be apparent that any suitable materials may be used, where the materials are biocompatible, inert, lightweight and low density. Preferably the materials have a liquid phase that may be controllably converted into a solid phase by a stimulus.

Generally speaking, after the material 200 has been delivered, the process 400 determines whether the appropriate amount of the material 200 has been delivered, e.g., whether the material has completely or sufficiently filled the LAA.

If the appropriate amount of the material 200 has been delivered, the process enters a second stage (indicated by block 408) to convert the material from a liquid phase to a solid phase. Specifically, the material within the LAA 102 is actively converted from a liquid phase to a solid phase, where active conversion refers to using a controllable mechanism to initiate conversion from the liquid phase to the solid phase. An example active mechanism is the introduction of a catalyst material into the LAA that induces a solid phase in the material 200, e.g., where that catalyst is formed of another biocompatible, inert material.

Another example technique for actively converting the material 200 within the LAA 102 from a fluid to a solid phase is by applying an electrical current, heat or light to induce the phase change in the material 200.

By using an active mechanism, the medical professional can more accurately control when the injected material will be solidified, which helps reduce the risk of embolism during the procedure and which also allows the medical professional to better control the amount of material inserted into the LAA. The latter is important for maximizing the amount of LAA volume closed off.

Non-active techniques for liquid-to-solid phase conversation are also contemplated. These include transitions that occur naturally over time, e.g., in response to body temperature, or in response to blood entering the LAA.

FIGS. 3A-3D illustrate various examples apparatuses for implanting transponders, each shown in a deployed stage. In FIG. 3A, the transponder unit 106 is inserted into the LAA 102 by the delivery catheter 190 and during the material injection process of FIG. 4, for example, between the first stage of injection and the second stage of active phase change. The transponder unit 106 may be inserted through another lumen channel in the catheter 190, while in other examples, the transponder unit 106 is maintained at a distal end of the catheter 190, for example, along with the occlusion device 194, which as shown in FIGS. 6a-6g can have an umbrella, butterfly, balloon or other design. FIG. 3B provides a more focused view of the configuration of FIG. 3A, showing the material 200 filling the entire volume and with the occlusion device 194 in place occluding the ostium 120 of the LAA 102.

FIG. 3C illustrates another example apparatus in which the transponder unit 106 is injected into the LAA 102 as part of the occlusion device 194. That occlusion device 194 includes a membrane structure 304 that covers the entire ostium 120 of the LAA 102 when deployed and is retained in place against the ostium 120 and the LAA 102 through the strut support structure 300. The struts 302 form anchor struts that are initially collapsed at least partially or fully along a longitudinal mainstay strut 306 until sufficiently deployed in the LAA 102. The struts 302 may then be deployed from which they will extend radially outward from the mainstay strut 306 to engage the inner wall 202 of the LAA 102. Preferably the struts 302 are in a staggered length and engage the inner wall 202 transversely, from the mainstay strut 306, and engage the inner wall 202 in an articulated fashion, in which longer struts engage portions of the inner wall 202 such that at least a portion of any lateral pulling force on the strut support structure 300 (i.e., pulling on the mainstay strut 306) will be counteracted by a lateral retaining force from these struts.

FIG. 3D illustrates an example similar to that of FIG. 3C, but showing the filler material 200 in place.

The struts 302 may be maintained against the inner wall 202 through means such as a spring force, pinch attachment, hooking end, etc.

The filtering membrane 304 may be made of biocompatible materials, such as, for example, ePFTE (e.g., Gortex®), polyester (e.g., Dacron®), PTFE (e.g., Teflon®), silicone, urethane, metal fibers, or other biocompatible polymers.

The membrane 304 may be impermeable to blood ingress. In other examples, the membrane 304 may be porous allowing blood to flow therethrough while blocking or inhibiting the passage of thrombus, clots, or emboli formed within the atrial appendage from entering the atrium of the heart and, the patient's bloodstream. Using a permeable membrane may reduce the risk of leakage about the periphery of the filtering membrane, or of dislodgement of the occlusion device that may result from the exertion of pressure against the surface of the occlusion device. Allowing the blood flow through and across the membrane 304 may relieve this pressure, sufficiently and in a controlled manner, to reduce such leakage or dislodgement. Tissue in-growth may additionally secure the occlusion device 194 to the opening of the LAA 102. More particularly, the growth of tissue may occur along the outer periphery of the occlusion device. This tissue growth, in cooperation with the pressure relief provided by the permeable structure, may provide additional means of reducing leakage about the periphery of the occlusion device. Tissue growth may eventually cover additional surface area of the membrane of the occlusion device.

Figure 5:
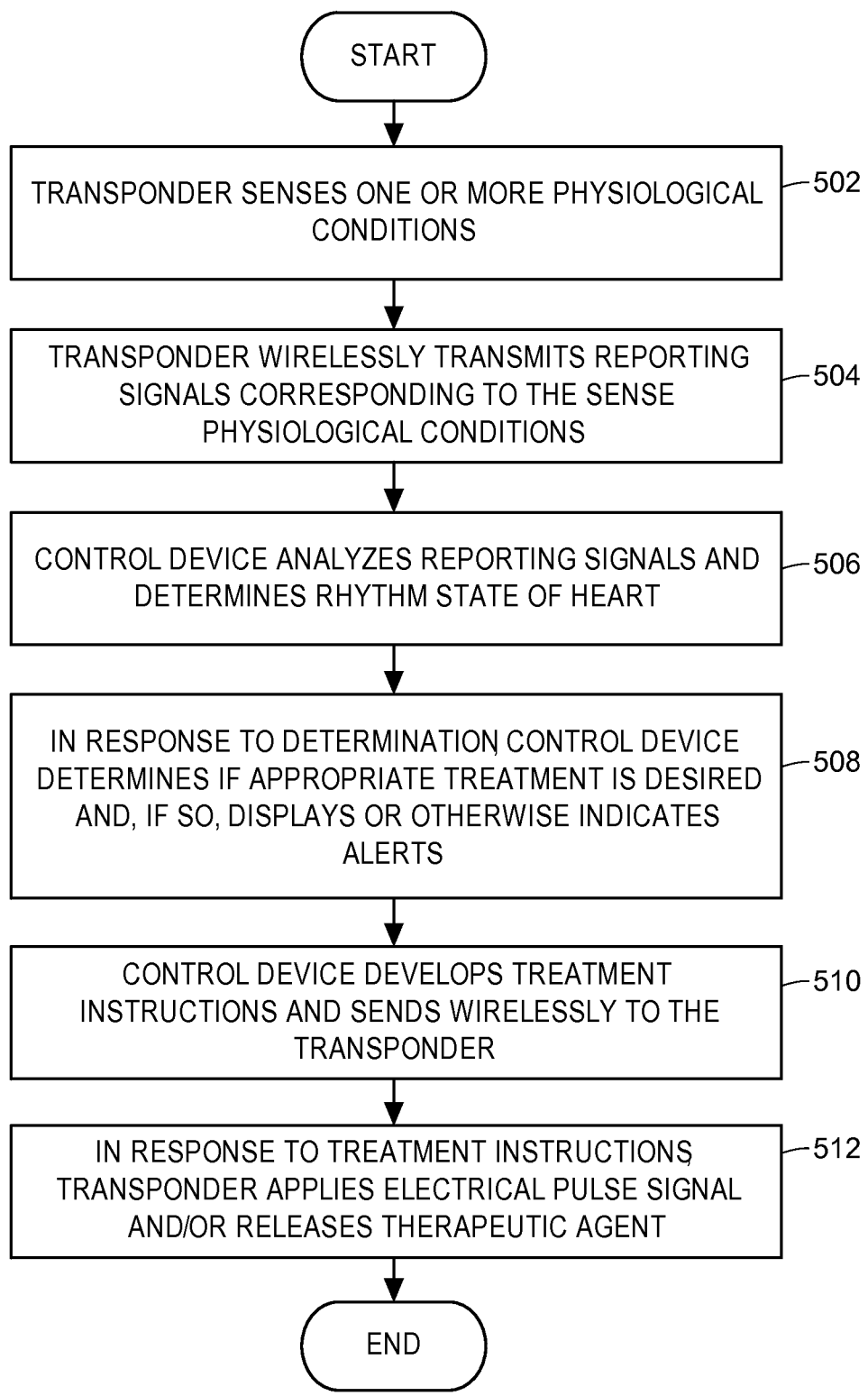
FIG. 5 illustrates a process for treating atrial fibrillation or atrial flutter.

FIG. 5 illustrates a process 500 for diagnosing atrial fibrillation or atrial flutter. At a block 502, a transponder unit senses one or more physiological conditions and then wirelessly transmits (e.g., block 504) reporting signals corresponding to those sensed physiological conditions to the control device, either directly (as discussed in relation to FIG. 5) or through a communication interface unit. At a block 506, the control device analyzes the received reporting signals and determines rhythm state of heart, e.g., whether the heart is experiencing SR, or AF. In response to the determination, the control device alerts the patient and/or the physician, via a block 508. In some examples, the process may further automatically develop treatment instructions and send those instructions wirelessly to the transponder, via a block 510.

Such treatment instructions may include instructions to the stage 182 for application of electrical pulse signals to heart through LAA and/or instructions to the stage 183 to deliver of a treatment agent into the LAA, which instructions may then be performed using the transponder device and the treatment stage 180, via block 512. For the later, the stage 183 is connected to an external, deployed therapeutic agent reservoir within the LAA or to reservoir within the transponder unit 106.

FIGS. 6a-6g illustrate various example occlusion devices that are configured to allow for injection of a filler material into the LAA and implantation of a transponder unit into the LAA for sensing and wireless communications.

In each of the examples illustrated by FIGS. 6A-6G, the inert filler material 200 may have any of the characteristics, features, or functions described in the examples above.

Figure 6A:
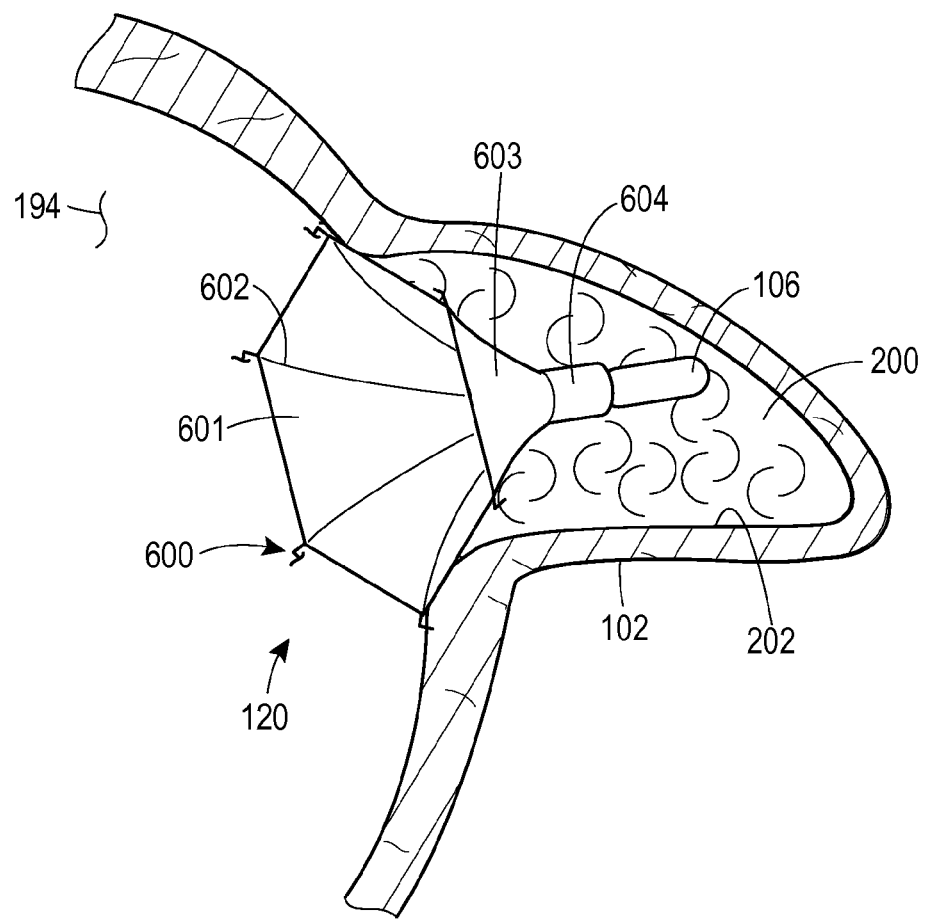
FIGS. 6A-6G illustrate various example occlusion devices that may be used in the apparatus of claim 1 to close off the ostium of the LAA.

FIG. 6A illustrates another example apparatus in which the occlusion device 194 has an inverted umbrella design and the transponder unit 106 is part of the occlusion device 194. The occlusion device 194 includes a membrane structure 601 that covers the entire ostium 120 of the LAA 102 when deployed and is retained in place against the ostium 120 and the LAA 102 through the strut support structure 600. The support ring 604, strut base 603, and filler material 200 maintains the struts 602 in the proper configuration. The struts 602 may be configured for attachment to the walls of the ostium 120 on the outer sides thereof through similar means as with struts 302 in FIG. 3C above.

The struts 602 are initially collapsed at least partially or fully collapsed along the longitudinal axis of the catheter 190 until the delivery sheath causes the struts 602 to extend radially outward and engage the outer wall of the ostium 120.

Figure 6B:
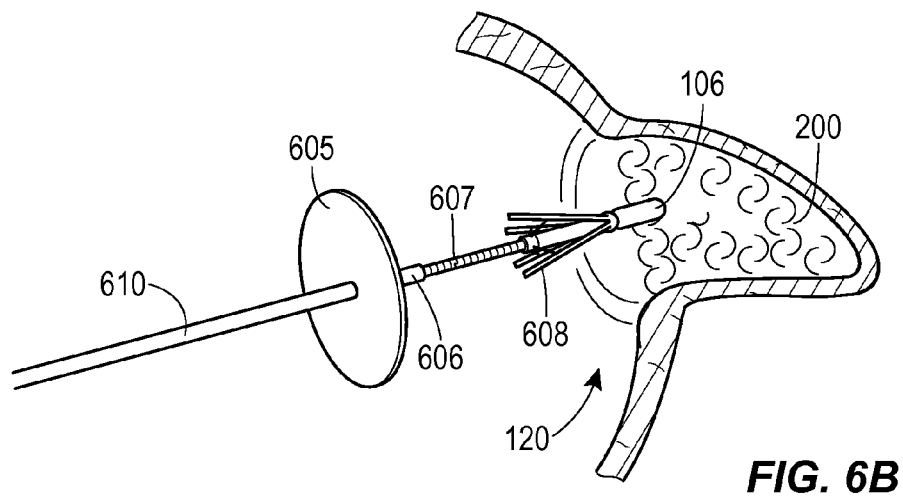
Figure 6C:
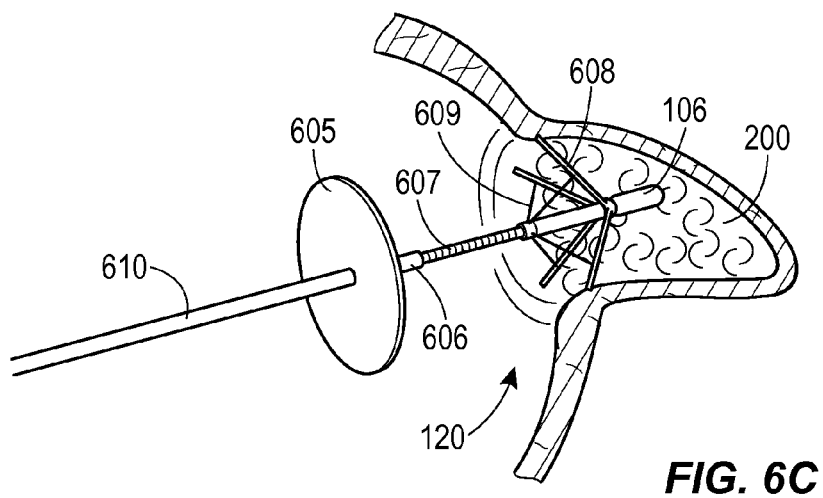
Figure 6D:
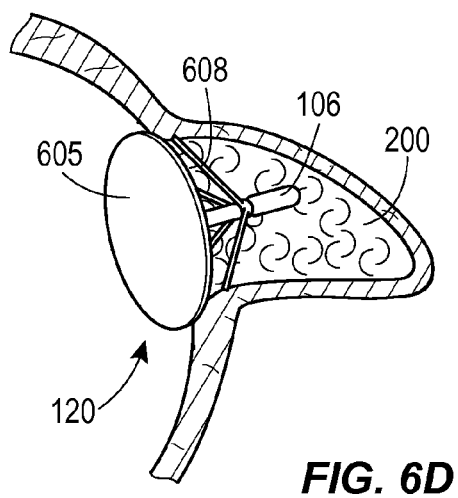

FIG. 6D illustrates another example apparatus in which the occlusion device 194 has an umbrella design. In some examples, the membrane structure 605 is drawn up against the ostium 120 by ratcheting the membrane structure along pole 610, shown in FIG. 6B. Shown in FIG. 6C, the pawl mechanism 606 engages teeth 607 on pole 610 and is moved forward to snugly position the membrane structure 605 across the ostium 120. The filler material 200 provides additional support, in conjunction with the strut support structure comprised of struts 608, to help maintain the membrane structure 605 in place.

FIGS. 6B-6C illustrate a method of delivery and deployment for the example apparatus of FIG. 6D. The umbrella opening structure 609 can be pushed to the open position (by a surgeon) or have a spring loaded mechanism to push the struts 608 to the open position. The ends of the umbrella struts 608 engage the LAA wall around the ostium 120 and prevent the umbrella design strut support structure from being withdrawn from the LAA.

Figure 6E:
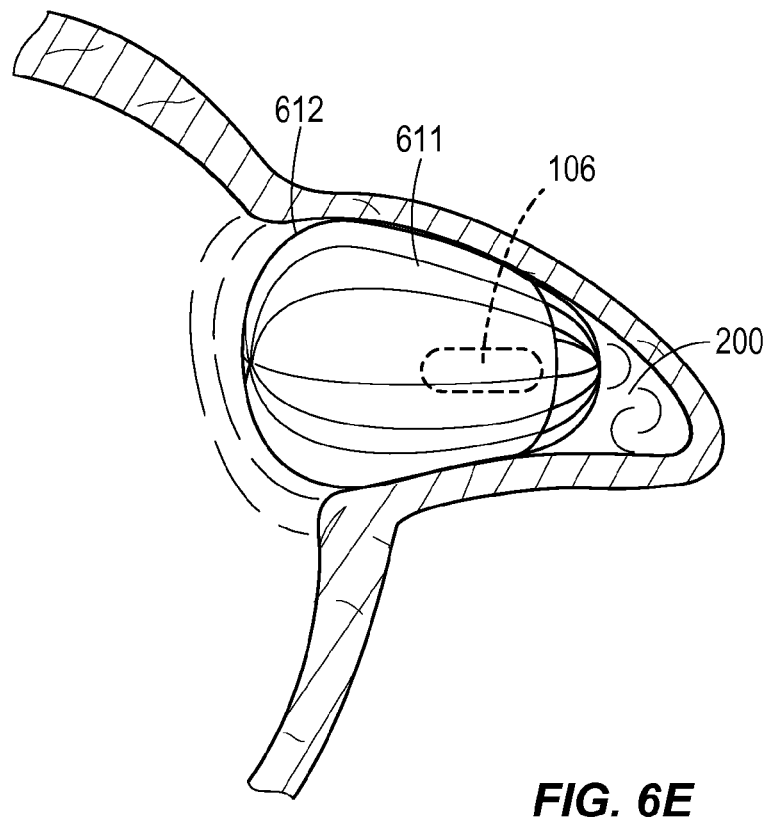

FIG. 6E illustrates another example apparatus in which the occlusion device 194 has a balloon design. The transponder unit 106 is embedded within the balloon occlusion device 194 in inflation material 611. The balloon 612 may be made from a compliant or non-compliant polymer, examples of which include silicone, polyethylene, polyurethane, and PET. The outside surface of the balloon may contain a material to induce fibrosis.

Inflation material 611 can be gas, fluid or gel that is injected under pressure through the delivery catheter 190. The inflation material could also be a polymer that can be hardened. The inflation material can also contain a radiopaque dye or other visualizable media.

Figure 6F:
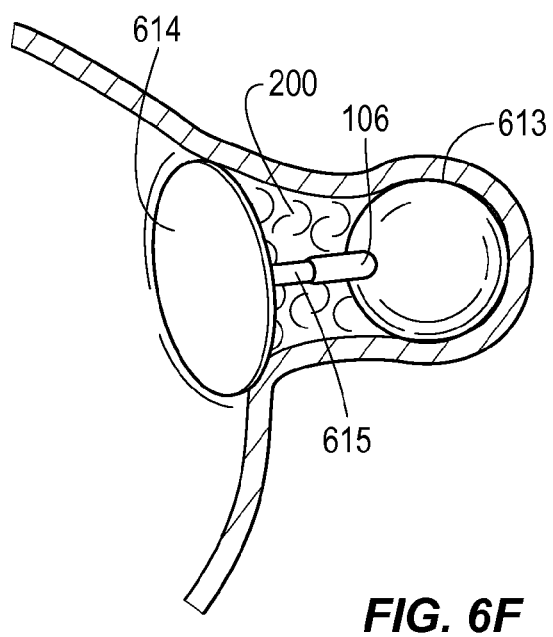

FIG. 6F illustrates another example apparatus in which the occlusion device 194 that utilizes an anchor balloon design. In one example, the balloon 613 expands within the LAA and secures the membrane structure 614 in place. In an alternative example, the balloon 613 is expanded prior to complete placement within the LAA, and the expanded balloon is then inserted into the distal end of the LAA cavity. The transponder 106 is attached to connecting rod 615 which is itself fixedly attached to and in between both the balloon 613 and the membrane structure 614.

In some examples, the transponder unit 106 may be conductively paired with the interior LAA wall 202 through conductive balloon 612. In alternative examples, the balloon 612 does not provide a conductive channel and instead serves only to provide support and stability for the occlusion device 194 and transponder unit 106. The balloon and filler material may be the same as described above with regards to the example illustrated in FIG. 6E.

Figure 6G:
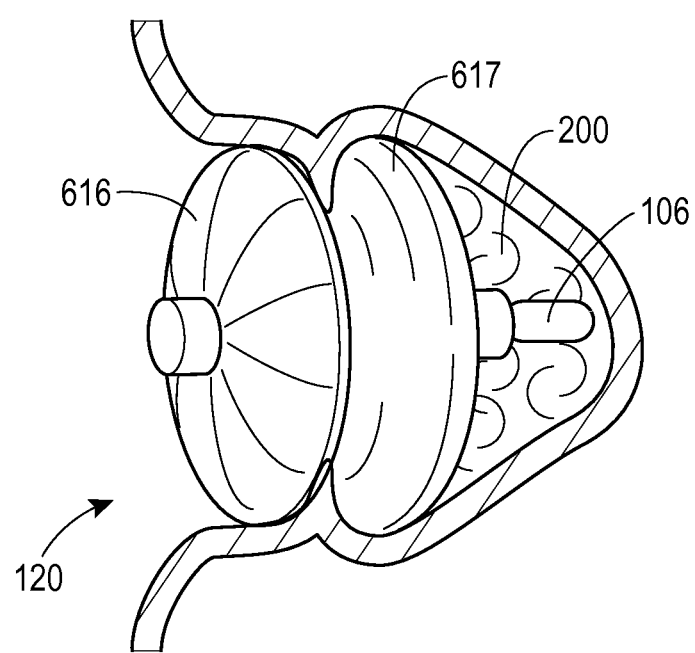

FIG. 6G illustrates another example apparatus in which the occlusion device 194 is of a butterfly design. Membrane structure 616 is secured in place by the anchor balloon 617 and positioned across the ostium 120. The outer edge of the membrane structure 616 may be directly engaged with the atrial wall surrounding the ostium 120. The anchor balloon 617 is initially collapsed and later expanded once inserted into the LAA. The transponder unit 106 is attached to the anchor balloon 617 and embedded in filler material 200 within the LAA.

Certain examples may be better suited for certain individual characteristics, such as the size and shape of the ostium 120 and LAA 102. The umbrella design illustrated in FIGS. 6A-6D and the balloon design illustrated in FIG. 6E may be better suited where the interior wall of ostium 120 is small such that it does not form a ledge on the interior of the LAA 102. The umbrella and balloon design examples of FIGS. 6A-6D and 6E, respectively, are further advantageous as being adaptable to fit a wide range of LAA sizes and shapes, providing near-universal fit. The anchor balloon design of FIG. 6F may be design more suited for where the distal end of the LAA 102 is larger. Alternatively or additionally, the anchor balloon can serve to expand the distal end of the LAA 102 to more securely engage the anchor inside the LAA. The butterfly design illustrated in FIG. 6G may be more effective where the size of the ostium 120 and the shape of the LAA 102 coincide such that the interior ostium wall 120 forms a ledge against which an anchor-structure may engage along the interior of the LAA 102.

Certain examples may additionally be advantageous as providing more rigid placement across the ostium 120, or alternatively, more flexible placement adaptable to movement of the ostium 120 and LAA 102.

Certain examples may additionally provide a simpler deployment procedure than others. In one example, the inverse-umbrella structure of FIG. 6A requires just a two step deployment process, involving the opening of the umbrella-shaped membrane structure 605 and the securing of the membrane structure across the ostium. This may be advantageous over other more complicated processes, such as the three step deployment example illustrated in FIGS. 6B-6D.

In some examples, the filler material is injected into the LAA prior to deployment of the occlusion device 194 and transponder unit 106. In alternative examples, the filler material is injected after the occlusion device and transponder unit have been deployed and secured into place. In the latter, the filler material might be injected through a delivery catheter operatively coupled to an injection mechanism on the occlusion device 194.

In any of the design described above, the LAA 102 might first be evacuated of thrombi through the use of an aspiration catheter or other aspirational means prior to injection of the filler material 200. Alternatively, the filler material 200 might be injected without prior aspiration. In both cases, the filler material serves to obliterate the left atrial appendage space.

Although the present techniques are described for use in the LAA, they may be also be implemented on the right atrial appendage or more generally in any vessel or aperture in the body in which blood is permitted to flow therethrough, in which blood clots may be formed and thus it desired to prevent such formations from embolizing and entering into the blood stream.

More broadly, while the above techniques have been described with reference to patients with AF or atrial flutter, the present application is not limited to this or any particular AF patient. The present techniques, for example, may be applied to arterial or venous aneurysms, etc.

Various blocks, operations, and techniques described above may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any computer readable memory such as on a magnetic disk, or other storage medium, in a RAM or ROM or flash memory of a computer, processor, hard disk drive, optical disk drive, tape drive, etc.

Stored on any one or on a combination of computer readable media, the present invention thus may include software for controlling hardware (e.g., a computer) capable of executing instructions stored on the computer readable medium and for enabling that hardware to interact with a human user. Such software may include, but is not limited to, device drivers, operating systems and user applications, such as development tools. Such computer readable media further includes the computer program product of the present invention for performing the inventive method of the present invention. The computer code devices of the present invention can be any interpreted or executable code mechanism, including but not limited to scripts, interpreters, dynamic link libraries, Java classes, and complete executable programs. Moreover, parts of the processing of the present invention may be distributed for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional component circuits, as will be readily apparent to those skilled in the art.

Moreover, while the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

Thus, although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

What is claimed is:

1. An implantable apparatus for blocking a left atrial appendage, the apparatus comprising:

an occlusion device having a positioning stage in which the occlusion device is collapsed for positioning the occlusion device at an opening of the left atrial appendage, the occlusion device having a cover that in a deployed stage encloses the opening and a strut support structure that in a deployed stage fixedly engages the cover to enclose the opening;

a transponder unit configured to sense one or more physiological conditions and configured to wirelessly transmit sensed measurements of the one or more physiological conditions to an external receiver, wherein the transponder unit is a multimodal device having a sensing mode in which the one or more physiological conditions are sensed and a treatment mode in which the transponder unit performs a treatment operation in the left atrial appendage; and a biocompatible, inert material in liquid phase inserted into the left atrial appendage, wherein the biocompatible, inert material freely suspends the transponder unit within the left atrial appendage.

2. The implantable apparatus of claim 1, wherein the inert material is maintained in the liquid phase within the left atrial appendage until an activation event is triggered that converts the biocompatible, inert material into a solid phase.

3. The implantable apparatus of claim 1, wherein the transponder unit is configured to simultaneously sense rhythm of the atria, pressure, transthoracic impedance, temperature, and oxygen saturation as the one or more physiological conditions.

4. The implantable apparatus of claim 1, wherein the transponder unit is further configured to simultaneously sense pH within the left atrial appendage.

5. The implantable apparatus of claim 1, wherein the transponder unit is passively powered by a power storage device within the transponder unit, the power storage device being inductively powered from an external inductive power source.

6. The implantable apparatus of claim 1, wherein the treatment operation is the application of an electrical signal to the left atrial appendage to alter the heartbeat rhythm of the heart.

7. The implantable apparatus of claim 1, wherein for the treatment operation is the release, by the transponder unit, of a pharmaceutical agent into the left atrial appendage for treatment of atrial fibrillation or heart failure.

8. The implantable apparatus of claim 1, wherein the one or more the physiological conditions comprises core body temperature.

9. The implantable apparatus of claim 1, further comprising an implantable interface unit that communicates with the transponder unit to receive reporting signals corresponding to the sensed measurements, wherein the implantable interface unit is implantable within the body of a subject.

10. The implantable apparatus of claim 9, wherein the implantable interface unit has a power supply mode in which the implantable interface unit inductively recharges the transponder unit.

11. The implantable apparatus of claim 9, wherein the implantable interface unit communicates instructions to program operation of the transponder unit.

12. The implantable apparatus of claim 1, further comprising an external interface unit that communicates with the transponder unit to receive the reporting signals, wherein the external interface unit is external to the body of a subject.

13. The implantable apparatus of claim 12, wherein the external interface unit has a power supply mode in which the external interface unit inductively recharges the transponder unit.

14. The implantable apparatus of claim 12, wherein the external interface unit communicates instructions to program operation of the transponder unit.

15. The implantable apparatus of claim 1, wherein the one or more physiological conditions comprise at least one of rhythm of the atria, pressure, transthoracic impedance, temperature, oxygen saturation, or pH.

* * * * *

UNITED STATES PATENT AND TRADEMARK OFFICE
CERTIFICATE OF CORRECTION

PATENT NO. : 9,011,551 B2  
APPLICATION NO. : 13/546662  
DATED : April 21, 2015  
INVENTOR(S) : Hakan Oral et al.

Page 1 of 1

It is certified that error appears in the above-identified patent and that said Letters Patent is hereby corrected as shown below:

<u>In the Claims:</u>

At Column 12, line 41, "for the" should be -- the --.

At Column 12, line 46, "more the" should be -- more --.

Signed and Sealed this
Twenty-sixth Day of April, 2016

Michelle K. Lee
*Director of the United States Patent and Trademark Office*